United States Patent [19]

Droste et al.

[11] 4,282,389
[45] Aug. 4, 1981

[54] PROCESS FOR THE SIMULTANEOUS MANUFACTURE OF PURE MTBE AND A SUBSTANTIALLY ISOBUTENE-FREE MIXTURE OF $C_4$-HYDROCARBONS

[75] Inventors: Wilhelm Droste; Fritz Obenaus, both of Marl, Fed. Rep. of Germany

[73] Assignee: Chemische Werke Hüls A.G., Marl, Fed. Rep. of Germany

[21] Appl. No.: 100,058

[22] Filed: Dec. 4, 1979

[30] Foreign Application Priority Data

Dec. 13, 1978 [DE] Fed. Rep. of Germany ....... 2853769

[51] Int. Cl.$^3$ ............................................. C07C 41/12
[52] U.S. Cl. ..................................... 568/697; 203/28; 203/75; 203/78; 203/82; 203/84; 568/699
[58] Field of Search ................... 568/697, 699; 203/28, 203/71, 73–75, 77, 78, 80, 81, 82, 84

[56] References Cited

U.S. PATENT DOCUMENTS 3,940,450  2/1976  Lee ....................................... 568/699
4,148,695  4/1979  Lee et al. ............................. 568/699

OTHER PUBLICATIONS

Chemical & Engineering News, Jun. 25, 1979, pp. 35 & 36.
Chemical & Engineering News, Aug. 27, 1979, p. 9.
Chemical & Engineering News, Dec. 17, 1979, p. 7.
Chemical & Engineering News, Dec. 24, 1979, p. 7.
Chemical & Engineering News, Jul. 14, 1980, p. 26.
Chemical & Engineering News, Jan. 26, 1981, p. 14.

Primary Examiner—Frank Sever
Attorney, Agent, or Firm—Gilbert L. Wells

[57] ABSTRACT

A process for the simultaneous manufacture of pure methyl tertiary butyl ether (MTBE) and a substantially isotubene-free mixture of $C_4$-hydrocarbons, by reacting the isobutene contained in the mixture of $C_4$-hydrocarbons with excess methanol in the liquid phase at elevated temperatures on strongly acid, macroporous, organic ion exchange resins.

The process has the following steps:
(a) methanol and isobutene are reacted in a molar ratio of 2:1 to 5:1 at temperatures between 30° and 100° C.;
(b) the unconverted hydrocarbons are then removed as the top product under a pressure of 2 to 10 bars from a first rectification column;
(c) the bottom product from this first column is rectified in a second column under normal pressure or under a slight excess pressure of up to 2 bars at the top of the column, the bottom product of this rectification is recycled to reaction zone (a), if necessary, after separating off a portion of the tertiary butanol formed and the $C_8$-olefins; and
(d) the distillate from this second column is rectified in a third rectification column under a pressure of 5 to 30 bars, the distillate thus obtained is recycled into the feed to the second column and pure methyl tertiary butyl ether is withdrawn from the bottom of the third column.

6 Claims, 1 Drawing Figure

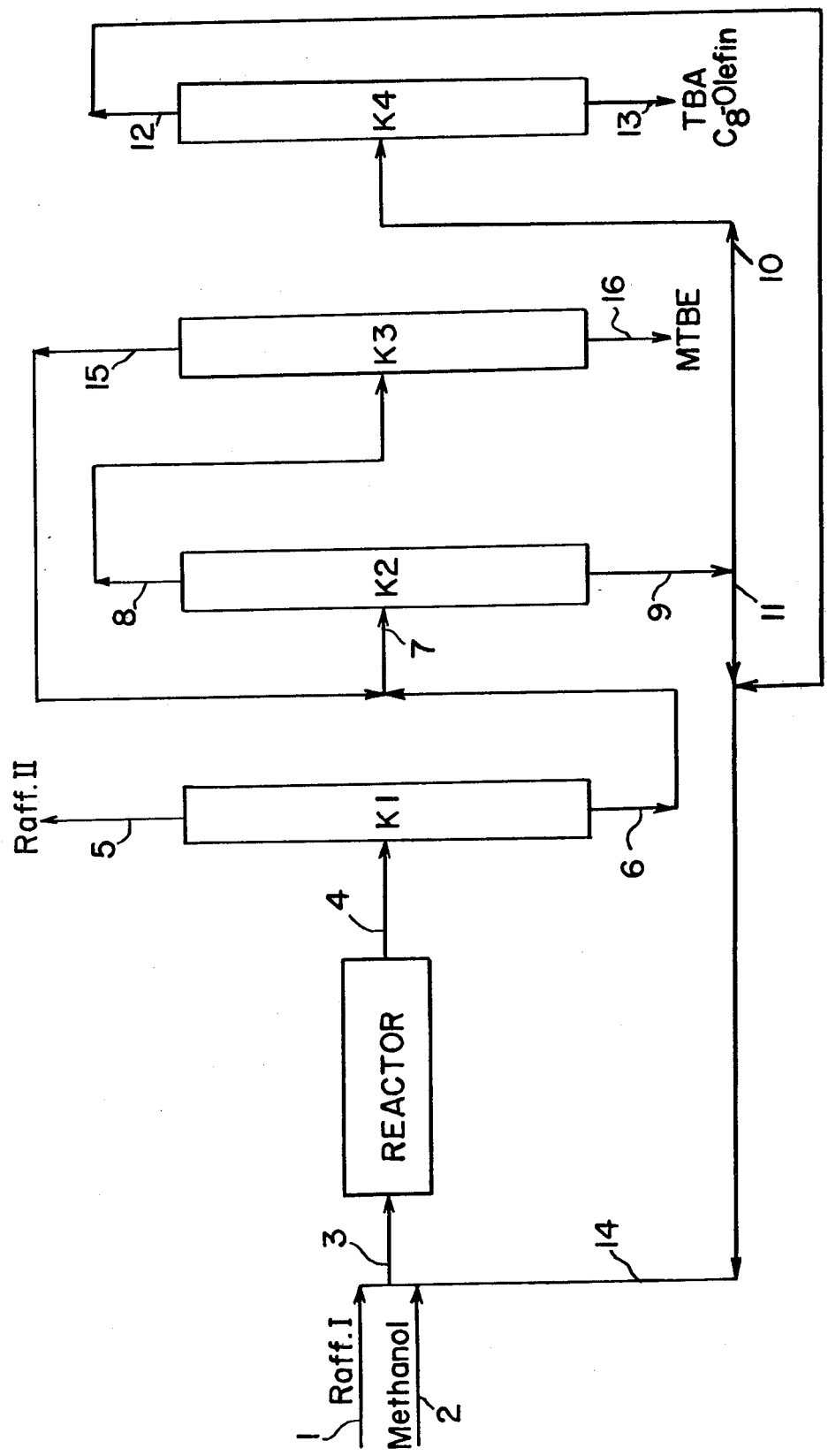

PROCESS FOR THE SIMULTANEOUS MANUFACTURE OF PURE MTBE AND A SUBSTANTIALLY ISOBUTENE-FREE MIXTURE OF $C_4$-HYDROCARBONS

CROSS REFERENCES TO RELATED APPLICATIONS

Applicants claim priority under 35 USC 119 for application No. P 28 53 769.1, filed Dec. 13, 1978 in the Patent Office of the Federal Republic of Germany.

The disclosure of assignee's copending application Ser. No. 974,550, filed Dec. 29, 1978 now U.S. Pat. No. 4,219,678 is incorporated herein.

BACKGROUND OF THE INVENTION

The field of the invention is the preparation of methyl tertiary butyl ether (MTBE) by the catalytic addition of methanol to isobutene. The state of the art of this preparation may be ascertained by reference to U.S. Pat. Nos. 2,480,940; 2,922,822; 3,121,124; 3,482,952; 3,726,942; 3,940,450 and 4,039,590, the disclosures of which are incorporated herein.

It is known that methyl tertiary butyl ether (MTBE) can be manufactured by an acid catalyzed addition reaction of methanol with isobutene. Catalysts which have become widely used for the acid catalyzed addition reaction are sulphonated organic resins, such as disclosed in U.S. Pat. No. 2,480,940, and especially the sulphonated polystyrene resins crosslinked with divinylbenzene, as disclosed in U.S. Pat. No. 3,922,822, which can be of a gelatinous nature or can possess a sponge structure with macropores, in order to increase the surface area and thus to increase the rate of reaction. British Pat. No. 957,000, Example 8, and U.S. Pat. No. 3,482,952 disclose the method of increasing the surface area.

Since the reaction between methanol and isobutene proceeds very selectively, it is in general not pure isobutene, but an isobutene-containing mixture of hydrocarbons which is employed. In particular, the crack $C_4$ hydrocarbon cut freed from butadiene—that is to say the so-called raffinate I—is employed for the reaction. However, other isobutene-containing mixtures of $C_4$-hydrocarbons can also be used such as disclosed in U.S. Pat. Nos. 3,121,124 and 4,039,590.

When raffinate I is employed for the manufacture of MTBE, the unconverted residue of the hydrocarbon mixture is termed raffinate II. When raffinate II is employed as the starting material for the manufacture of further products, such as, for example, maleic anhydride or methyl ethyl ketone, or for obtaining 1-butene or in polymerization reactions, the standards of quality demanded of raffinate II are high. In particular in the case of its use for obtaining 1-butene from raffinate II by distillation, the isobutene content of raffinate II must be substantially less than 1% and preferably even less than 0.25 percent by weight, since the isobutene cannot be separated off from 1-butene by distillation and therefore remains in its entirety in the 1-butene. However, a maximum content of isobutene of less than 0.25 percent by weight in raffinate II means that when the isobutene is removed by reaction an isobutene conversion of at least 99.75% must be achieved.

When isobutene is reacted with methanol to give MTBE, the product is not pure MTBE, but only MTBE/methanol azeotrope and methanol. Solutions to the problems of separating the methanol from the MTBE have already been proposed, for example by an extractive distillation with dimethylsulphoxide, as disclosed in Japanese published application No. 73-00509, now Japanese Pat. Sho No. 48-509 or by a water wash, as disclosed in British Pat. No. 1,369,889, and U.S. Pat. No. 3,726,942. In U.S. Pat. No. 3,940,450, the separation of methanol and MTBE is carried out in two stages using pentane as an auxiliary material. All of these processes are relatively involved, since the auxiliary materials employed have to be removed again virtually completely from the MTBE and the methanol. The isobutene conversions achievable are unsatisfactory. In the process according to U.S. Pat. No. 3,726,942, only 70% of the isobutene is converted to MTBE, while according to U.S. Pat. Nos. 3,940,450, a MTBE yield of 80% is achieved.

U.S. Pat. No. 3,979,461 and 4,071,567 describe processes for the manufacture of MTBE by reacting isobutene containing mixtures of $C_4$-hydrocarbons with methanol in two reaction zones. However, even with these two processes, adequately high isobutene conversions are not achievable in a conrolled manner, where the lowest isobutene content is given as 0.27% in Example 6 of U.S. Pat. No. 3,979,461. In order to achieve high isobutene conversions in the manufacture of methanol-free MTBE it is necessary to carry out the reaction in one of the two reaction stages using high reactor temperatures or a molar excess of isobutene over methanol. As a result of this, however, oligomerization products of isobutene, dimerization and trimerization, also form in addition to MTBE and, in an undesired manner, a considerable isomerization of the $C_4$-olefins in the mixture of hydrocarbons takes place. In any subsequent distillation which may be carried out to isolate 1-butene from the $C_4$ mixture, the isomerization of 1-butene to 2-butene has the effect of a product loss.

U.S. Pat. No. 4,219,678 does indeed describe a one-stage process for the manufacture of MTBE, in which the working up of the reaction mixture is carried out without the use of auxiliary materials and which does not have the abovementioned disadvantages, such as the formation of oligomerization products of isobutene and isomerization of the unconverted $C_4$-olefins, but the maximum isobutene conversion which can be achieved is only about 98.6% so that the residual $C_4$ mixture (raffinate II) contains more than 1% of isobutene.

SUMMARY OF THE INVENTION

Having in mind the limitations of the prior art, it is an object of the present invention to provide a simple process for the simultaneous manufacture of pure MTBE and isolation of a virtually isobutene-free mixture of $C_4$-hydrocarbons wherein isobutene content of less than 0.25 percent by weight is achieved for specific applications.

According to the present invention, pure MTBE and a substantially isobutene-free mixture of $C_4$-hydrocarbons is manufactured simultaneously by reacting the isobutene contained in the mixture of $C_4$-hydrocarbons with excess methanol in the liquid phase at elevated temperatures on strongly acid, macroporous, organic ion exchange resins.

The following steps are used in the process:
(a) methanol and isobutene are reacted in a molar ratio of 2:1 to 5:1 at temperatures between 30° and 100° C.;

(b) the unconverted hydrocarbons are then removed as the top product under a pressure of 2 to 10 bars from a first rectification column;

(c) the bottom product from this first column is rectified in a second column under normal pressure or under a slight excess pressure of up to 2 bars at the top of the column, the bottom product of this rectification is recycled to reaction zone (a), if necessary, after separating off a portion of the tertiary butanol formed and the $C_8$-olefins; and (d) the distillate from this second column is rectified in a third rectification column under a pressure of 5 to 30 bars, the distillate thus obtained is recycled into the feed to the second column and pure methyl tertiary butyl ether is withdrawn from the bottom of the third column.

The molar ratio of methanol to isobutene in the feed mixture is in the range of 2:1 to 5:1. Below a molar ratio of 2:1 it is possible to achieve the desired high isobutene conversion of much more than 99% ony when the reaction temperature is substantially lowered at the same time. However, a substantial lowering of the reaction temperature has the effect of reducing the rate of reaction to an extent which virtually precludes practical application.

Above a molar ratio of 5:1, the process becomes uneconomical, because of the rising costs for separating off the methanol. The amounts of methanol which have to be cycled during the distillation are too large and, in addition, the effect of the increase in the conversion becomes ever smaller as the methanol excess becomes larger. In order to enable the isobutene content of raffinate II to be reduced to below 0.25 percent by weight, this being demanded in practice for many purposes, a molar excess of methanol relative to isobutene of about 2.5:1 to 4:1 is preferably chosen.

The reaction temperature for the reaction of methanol with isobutene is between about 30° and 100° C. In general, the reaction is carried out in a temperature range of about 50° to 100° C., in order to obtain a good rate of reaction. It has proved particularly advantageous to keep the reaction temperature in the front section of the catalyst bed at between 50° and 100° C. and to maintain a temperature of below 50° C. down to a temperature of about 30° C. in the subsequent section which comprises at least one-third of the reaction zone.

The dwell time of the reaction mixture on the catalyst depends on the activity of the catalyst and must therefore be determined individually for each catalyst. When the highly active macroporous ion exchange resins are used as catalysts, the dwell time is in general between 10 and 60 minutes.

BRIEF DESCRIPTION OF THE DRAWING

The FIGURE of the drawing is a flow sheet showing the process of the present invention.

DESCRIPTION OF THE PREFERRED EMBODIMENTS

With particular reference to the drawing, the feed mixture, for example, raffinate I, and methanol are shown being fed through lines 1 and 2 respectively and through line 3 into the reactor. The reaction mixture which leaves the reactor is fed through line 4 to a pressure column (K1). In this column, the $C_4$-hydrocarbons which do not participate in the reaction and small amounts of unconverted isobutene (raffinate II) are drawn off at the top (line 5), while the MTBE formed during the reaction and excess methanol are obtained at the bottom. In accordance with the pressure set up during rectification, the distillate contains small amounts of methanol, which forms an azeotrope with the $C_4$-hydrocarbons. This methanol can be removed from the top product (raffinate II) by extraction with water. The pressure at the top of column K1 is between 2 and 10 bars and in particular between 6 and 8 bars, since the condensation of the distillate with cooling water can be operated particularly economically in this range.

The bottom product from column K1 is fed via lines 6 and 7 to column K2. The bulk of the methanol employed in excess in the reaction is obtained at the bottom of column K2, in some cases together with small amounts of tertiary butanol (TBA) and $C_8$-olefins, which can form as by-products in the reaction, and methanol is withdrawn via line 9. While in the indicated range of reaction conditions, $C_8$-olefins form only in traces, the amount of TBA formed depends on the water content of the methanol employed and of the mixture of hydrocarbons. This bottom product from column K2 is fed back into the reaction via lines 11 and 14. However, before recycling into the reaction, a partial stream must, if necessary, be fed, for the purpose of working up, via line 10 to column K4, where the by-products TBA and $C_8$-olefins formed during the reaction are separated off. The proportion of the product to be worked up in column K4 depends on the amount of TBA and $C_8$-olefins, which on one hand are formed and on the other hand can remain in the reaction cycle. TBA and $C_8$-olefin proportions of at least 1 to 2 percent by weight in the recycled methanol are permissible, so that the product fed via line 10 to column K4 is always restricted to a small porportion of the bottom product obtained in column K2. In column K4, the high-boiling products TBA and $C_8$-olefins are removed from the bottom via line 13. The top product of column K4 is combined, via lines 12 and 14, with the methanol from line 2 and fed back into the reactor.

The top product from column K2 is fed via line 8 to the pressure column K3, where pure MTBE is obtained as the bottom product (line 16) and a MTBE/methanol azeotrope, in which the proportion of methanol corresponds to the pressure set up in the column, is obtained as the top product. The top product from column K3 is fed back to column K2, via lines 15 and 7. In order to reduce the proportion of MTBE in the top product from column K3 and thus to reduce the amount fed back into the feed to column K2, the pressure in column K3 should be chosen to be as high as possible. The pressure in column K3 should, therefore, be in the range between 5 and 30 bars. The upper limit for the pressure is determined by purely economic considerations relating to the counterbalancing effect of energy costs and investment costs.

At the top of column K2, MTBE is distilled off at degrees of enrichment only up to that corresponding to the MTBE/methanol azeotrope. For this reason, the pressure in the column is kept as low as possible, in order to reduce the amount of methanol present in the azeotrope and thus to reduce the amount of top product from column K3 which is cycled. A technically reasonable and particularly economical procedure is to operate under normal pressure or under a top pressure of up to 2.0 bars.

By means of the process described above, it is possible to produce pure MTBE in a simple manner using only one reactor, with virtually complete conversion of the isobutene. A virtually complete conversion of the isobutene means that the mixture of $C_4$-hydrocarbons which does not participate in the reaction is substantially free from isobutene and can be employed for separating off pure 1-butene by distillation or for selective chemical reactions of the n-butene. The examples which follow serve to illustrate the process, but are not intended to restrict it in any way.

EXAMPLE 1

100.02 kg/hour of raffinate I, which contains 45.00 kg/hour of isobutene, 26.1 kg/hour of 1-butene and 0.02 kg/hour of water, 27.88 kg/hour of methanol, which contains 0.02 kg/hour of water and 76.45 kg/hour of recycled methanol, which contains 0.09 kg/hour of $C_8$-olefins and 1.44 kg/hour of tert.-butanol, are fed, via line 1, line 2 and line 14, respectively, into a reactor which is packed with 220 l of strongly acid ion exchanger (macroporous, sulphonated polystyrene resin crosslinked with divinylbenzene) and from which, as a result of the incorporation of suitable cooling devices, the heat of reaction generated can be removed efficiently. The molar ratio of methanol to isobutene is 4:1.

At a temperature of 52° C. inside the catalyst bed, 99.71% of the isobutene is converted. The following products leave the reactor via line 4: 77.23 kg/hour of methanol, 0.13 kg/hour of isobutene, 55 kg/hour of a n-$C_4$-olefin/butane mixture (including 26.1 kg/hour of 1-butene), 70.29 kg/hour of MTBE, 0.10 kg/hour of $C_8$-olefins and 1.60 kg/hour of tert.-butanol.

In order to separate off the unconverted $C_4$-hydrocarbons, the reaction product is first fed to pressure column K1 (top pressure 6 bars), where a total of 55.00 kg/hour of a n-$C_4$-olefin/butane mixture, 0.13 kg/hour of isobutene and 2.18 kg/hour of methanol are taken off at the top of the column via line 5. The bottom product of column K1 has the following composition: 75.05 kg/hour of methanol, 70.29 kg/hour of MTBE, 0.10 kg/hour of $C_8$-olefins and 1.60 kg/hour of tert.-butanol, and is fed via lines 6 and 7 into column K2, which is operated under a pressure of 1.35 bars.

Together with the top product from column K3, which is recycled via lines 15 and 7, this gives a total feed to column K2 of 90.23 kg/hour of methanol, 88.11 kg/hour of MTBE, 0.10 kg/hour of $C_8$-olefins and 1.60 kg/hour of tert.-butanol.

Under a top pressure of 1.35 bars, a MTBE/methanol azeotrope containing 14.7% of methanol, which corresponds to a mixture of 88.11 kg/hour of MTBE and 15.18 kg/hour of methanol, is withdrawn at the top of column K2 via line 8.

A product of the following composition: 75.05 kg/hour of methanol, 0.10 kg/hour of $C_8$-olefins and 1.60 kg/hour of tert.-butanol, is withdrawn from the bottom of column K2 via line 9.

In order to prevent the $C_8$-olefins and the tert.-butanol becoming enriched in the reaction cycle, 10% of this product is fed via line 10 to column K4, while the remaining 90% is recycled via lines 11 and 14 directly into the reactor. 0.13 kg/hour of methanol, 0.16 kg/hour of tert.-butanol and 0.01 kg/hour of $C_8$-olefins are withdrawn as the bottom product from column K4, which is operated under normal pressure, via line 13. 7.38 kg/hour of methanol are obtained as the distillate and are withdrawn via line 12 and combined again with the bulk of the bottom run-off from column K2 (line 11), so that the total amount fed back into the reaction via line 14 has the following composition: 74.92 kg/hour of methanol, 0.09 kg/hour of $C_8$-olefins and 1.44 kg/hour of tert.-butanol.

The top product from column K2 is fed via line 8 to column K3, which has a top pressure of 30 bars. Under a pressure of 30 bars, the MTBE/methanol azeotrope contains 46% of methanol, so that 15.18 kg/hour of methanol and 17.82 kg/hour of MTBE are obtained at the top of column K3 and this product is recycled to column K2 via line 15. 70.29 kg/hour of MTBE with a purity of about 99.9 percent by weight are withdrawn from the bottom of column K3 via line 16.

Thus, 70.29 kg/hour of highly pure MTBE and 55.13 kg/hour of raffinate II containing 0.24% of isobutene (calculated methanol-free) are manufactured from 27.88 kg/hour of methanol and 100.02 kg/hour of raffinate I. No detectable losses of 1-butene occur during the reaction.

EXAMPLE 2

As a liquid mixture, 100.02 kg/hour of $C_4$ cut (raffinate I), which contains 45 kg/hour of isobutene, 26.1 kg/hour of 1-butene and 0.02 kg/hour of $H_2O$, 27.94 kg/hour of methanol, which contains 0.01 kg/hour of $H_2O$, and 37.03 kg/hour of a mixture of 36.51 kg/hour of methanol, 0.04 kg/hour of $C_8$-olefins and 0.48 kg/hour of tert.-butanol are fed, via line 1, line 2 and line 14, respectively, under an initial pressure of about 10 bars, into a reactor which is packed with 200 l of strongly acid ion exchanger (macroporous, sulphonated polystyrene resin crosslinked with divinylbenzene) and from which, as a result of the incorporation of suitable cooling devices, the heat of reaction generated can be removed efficiently. This corresponds to a molar ratio of 2.51:1 for methanol to isobutene. With a maximum temperature of about 80° C. in the front part of the reactor bed and a temperature of 40° C. in the final third of the catalyst bed, 99.76% of the isobutene is converted.

In order to separate off the unconverted $C_4$-hydrocarbons, the reaction product, which has the composition 38.86 kg/hour of methanol, 0.11 kg/hour of isobutene, 55.00 kg/hour of a n-$C_4$-olefin/butane mixture (including 26.1 kg of 1-butene), 70.37 kg/hour of MTBE, 0.05 kg/hour of $C_8$-olefins and 0.60 kg/hour of tert.-butanol, is then fed via line 4 to pressure column K1, where 55.00 kg/hour of a n-$C_4$-olefin/butane mixture, 0.11 kg/hour of isobutene and 2.18 kg/hour of methanol are withdrawn from the top of the column via line 5. Under the rectification conditions (top pressure 6 bars), methanol forms an azeotrope with the $C_4$-hydrocarbons. The bottom product from column K1 is withdrawn via line 6 and fed via line 7 into column K2, which is operated under a pressure of 1.35 bars. This product has the composition 36.68 kg/hour of methanol, 70.37 kg/hour of MTBE, 0.05 kg/hour of $C_8$-olefins and 0.60 kg/hour of tert.-butanol.

Together with the top product from column K3, which is recycled via lines 15 and 7, this gives a total feed to column K2 of 56.97 kg/hour of methanol, 117.71 kg/hour of MTBE, 0.05 kg/hour of $C_8$-olefins and 0.60 kg/hour of tert.-butanol. The MTBE/methanol azeotrope obtained as the top product from column K2 contains 14.7% of methanol, which corresponds to a mixture of 117.71 kg/hour of MTBE and 20.29 kg/hour of methanol. This product is fed via line 8 to column K3. A product of the following composition: 36.68 kg/hour of methanol, 0.05 kg/hour of $C_8$-olefins and 0.60 kg/hour of tert.-butanol is withdrawn from the bottom of column K2 via line 9.

In order to prevent the $C_8$-olefins and the tert.-butanol becoming enriched in the reaction cycle, 20% of this product is fed via line 10 to column K4, while the remaining 80% is recycled directly into the reactor, via lines 11, 14 and 3. 0.3 kg/hour of a product which contains, in addition to methanol, 0.01 kg/hour of $C_8$-olefins and 0.12 kg/hour of tert.-butanol is withdrawn (line 13) from the bottom of column K4, which is operated under normal pressure. At the same time, 7.17 kg/hour of methanol are obtained as the distillate. This methanol is again combined, via line 12, with the bulk of the bottom run-off from column K2 (line 11), so that the total amount recycled via line 14 into the reactor has the following composition: 36.51 kg/hour of methanol, 0.04 kg/hour of $C_8$-olefins and 0.48 kg/hour of tert.-butanol.

The top product from column K2 is fed via line 8 into column K3, which has a top pressure of 8.6 bars. Under a pressure of 8.6 bars, the MTBE/methanol azeotrope contains 30% of methanol, so that 20.29 kg/hour of methanol and 47.34 kg/hour of MTBE are obtained at the top of column K3; this product is recycled via line 15 into column K2. 70.37 kg/hour of MTBE with a purity of greater than 99.9 percent by weight are then obtained at the bottom of column K3 and are withdrawn via line 16.

Thus, 70.37 kg/hour of highly pure MTBE and 55.11 kg/hour of raffinate II containing 0.20% of isobutene (calculated methanol-free) are manufactured from 27.94 kg/hour of methanol and 100.02 kg/hour of raffinate I. No detectable losses of 1-butene occurred during the reaction.

EXAMPLE 3 100.02 kg/hour of raffinate I, which contains 45.00 kg/hour of isobutene, 26.1 kg/hour of 1-butene and 0.02 kg/hour of water, 28.04 kg/hour of methanol, which contains 0.02 kg/hour of water, and 63.71 kg/hour of recycled methanol, which contains 0.09 kg/hour of $C_8$-olefins and 1.44 kg/hour of tert.-butanol, are fed, via line 1, line 2 and line 14, respectively, into a reactor which is packed with 200 l of strongly acid ion exchanger (macroporous, sulphonated polystyrene resin crosslinked with divinylbenzene) and from which, as the result of the incorporation of suitable cooling devices, the heat of reaction generated can be removed efficiently. The molar ratio of methanol to isobutene is 3.51:1.

With a maximum temperature of about 80° C. in the front part of the catalyst bed and a temperature of 40° C. in the final third of the catalyst bed, 99.84% of the isobutene is converted. The following products leave the reactor via line 4: 64.62 kg/hour of methanol, 0.08 kg/hour of isobutene, 55.00 kg/hour of a n-$C_4$-olefin/butane mixture (including 26.1 kg/hour of 1-butene), 70.38 kg/hour of MTBE, 0.10 kg/hour of $C_8$-olefins and 1.60 kg/hour of tert.-butanol.

In order to separate off the unconverted $C_4$-hydrocarbons, the reaction product is first fed to pressure column K1 (top pressure 6 bars), where a total of 55.00 kg/hour of a n-$C_4$-olefin/butane mixture, 0.07 kg/hour of isobutene and 2.18 kg/hour of methanol are withdrawn from the top of the column via line 5. The bottom product from K1 has the composition: 62.44 kg/hour of methanol, 70.38 kg/hour of MTBE, 0.10 kg/hour of $C_8$-olefins and 1.60 Kg/hour of tert.-butanol, and is fed via lines 6 and 7 into column K2 which is operated under a pressure of 1.35 bars.

Together with the top product from column K3, which is recycled via lines 15 and 7, this gives a total feed to column K2 of 77.62 kg/hour of methanol, 88.20 kg/hour of MTBE, 0.10 kg/hour of $C_8$-olefins and 1.60 kg/hour of tert.-butanol.

Under a top pressure of 1.35 bars, a MTBE/methanol azeotrope containing 14.7% of methanol, which corresponds to a mixture of 88.20 kg/hour of MTBE and 15.18 kg/hour of methanol, is withdrawn from the top of column K2 via line 8.

A product of the following composition: 62.44 kg/hour of methanol, 0.10 kg/hour of $C_8$-olefins and 1.60 kg/hour of tert.-butanol, is withdrawn from the bottom of column K2 via line 9.

In order to prevent the $C_8$-olefins and the tert.-butanol becoming enriched in the reaction cycle, 10% of this product is fed via line 10 into column K4, while the remaining 90% is recycled directly into the reactor, via lines 11 and 14. 0.43 kg/hour of a bottom product which contains 0.01 kg/hour of $C_8$-olefins and 0.16 kg/hour of tert.-butanol, in addition to methanol, is withdrawn via line 13 from column K4, which is operated under normal pressure. 5.98 kg/hour of methanol are obtained as the distillate. This methanol is withdrawn via line 12 and recombined with the bulk of the bottom run-off from column K2 (line 11), so that the total amount recycled into the reaction via line 14 has the following composition: 62.18 kg/hour of methanol, 0.09 kg/hour of $C_8$-olefins and 1.44 kg/hour of tert.-butanol.

The top product from column K2 is fed via line 8 to column K3, which has a top pressure of 30 bars. Under a pressure of 30 bars, the MTBE/methanol azeotrope contains 46% of methanol, so that 15.18 kg/hour of methanol and 17.82 kg/hour of MTBE are obtained at the top of column K3 and this product is recycled into coloumn K2 via line 15. 70.38 kg/hour of MTBE with a purity of about 99.9 percent by weight are withdrawn from the bottom of column K3 via line 16.

Thus, 70.38 kg/hour of highly pure MTBE and 55.07 kg/hour of raffinate II containing 0.13% of isobutene (calculated methanol-free) are manufactured from 28.04 kg/hour of methanol and 100.02 kg/hour of raffinate I. No detectable losses of 1-butene occurred during the reaction.

We claim:
1. In a process for the simultaneous manufacture of pure methyl tertiary butyl ether and a substantially isobutene-free mixture of $C_4$-hydrocarbons, by reacting isobutene contained in a mixture of $C_4$-hydrocarbons with excess methanol in the liquid phase at elevated temperatures on strongly acid, macroporous, organic ion exchange resins, the improvement comprising:
(a) reacting said methanol and said isobutene in a molar ratio of 2:1 to 5:1 at temperatures of between about 30° and 100° C.;
(b) removing unconverted hydrocarbons as the top product under a pressure of 2 to 10 bars from a first rectification column;
(c) rectifying the bottom product from said first rectification column in a second column under a pressure of about normal pressure to a pressure of about 2 bars excess at the top of the second column and recycling the bottom product of said second column to step (a); and
(d) rectifying the distillate from said second column consisting essentially of an azeotrope of methanol and methyl tertiary butyl ether in a third rectifica- tion column under a pressure of about 5 to 30 bars without adding auxiliary material, recycling the distillate of said third column into the feed of said second column and withdrawing said pure methyl tertiary butyl ether from the bottom of said third column.

2. The process of claim 1, wherein a portion of tertiary butanol formed and $C_8$-olefins are separated from the bottom product of said second column by the use of a fourth column.

3. The process of claim 1, wherein the reaction of step (a) is carried out in a temperature range of about 50° to 100° C.

4. The process of claim 1, wherein the reaction of step (a) is carried out in the front section of a catalyst bed kept at a temperature of between 50° C. and 100° C. and in a subsequent section, which comprises at least one third of the reaction zone, the temperature is kept below 50° C. down to a temperature of about 30° C.

5. The process of claim 1, wherein methanol and isobutene are employed in a molar ratio of 2.5:1 to 4:1 in step (a).

6. The process of claim 5, wherein the top product of step (b) contains less than 0.25 percent by weight of isobutene.

* * * * *